(12) United States Patent
Joshi et al.

(10) Patent No.: US 8,471,039 B2
(45) Date of Patent: Jun. 25, 2013

(54) PROCESS FOR THE PREPARATION OF INDOLINE DERIVATIVES AND THEIR INTERMEDIATES THEREOF

(75) Inventors: Shreerang Joshi, Maharashtra (IN); Sachin Bhuta, Maharashtra (IN); Sanjay Talukdar, Maharashtra (IN); Sudhir Sawant, Maharashtra (IN); Deepak Venkataraman, Maharashtra (IN); Abhinay Pise, Maharashtra (IN); Shashikant Metkar, Maharashtra (IN); Dattatraya Chavan, Maharashtra (IN); Parven Kumar Luthra, Maharashtra (IN)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 13/392,564

(22) PCT Filed: Sep. 13, 2010

(86) PCT No.: PCT/IN2010/000607
§ 371 (c)(1),
(2), (4) Date: Feb. 27, 2012

(87) PCT Pub. No.: WO2011/030356
PCT Pub. Date: Mar. 17, 2011

(65) Prior Publication Data
US 2012/0165548 A1  Jun. 28, 2012

(30) Foreign Application Priority Data
Sep. 12, 2009 (IN) .......................... 1420/MUM/2009

(51) Int. Cl.
*C07D 209/08* (2006.01)

(52) U.S. Cl.
USPC .......................................... 548/507

(58) Field of Classification Search
USPC .......................................... 548/507
See application file for complete search history.

(56) References Cited

U.S. PATENT DOCUMENTS
5,387,603 A * 2/1995 Kitazawa et al. ............. 514/415

FOREIGN PATENT DOCUMENTS
EP  1806340 A1  7/2007
JP  4634580       1/2000
JP  2001199956 A  7/2001

OTHER PUBLICATIONS
International Search Report and Written Opinion (mailed Mar. 4, 2011).
Written Opinion (Mailed Mar. 2, 2011).

* cited by examiner

*Primary Examiner* — Shawquia Young
(74) *Attorney, Agent, or Firm* — Jeffrey S. Melcher; Manelli Selter PLLC

(57) ABSTRACT

Processes for the preparation of Silodosin and its intermediates comprising reductive amination of compound of Formula (VIII) with a compound of Formula (VII) or a compound of Formula (XV) in a suitable solvent using a reducing agent.

12 Claims, No Drawings

PROCESS FOR THE PREPARATION OF INDOLINE DERIVATIVES AND THEIR INTERMEDIATES THEREOF

FIELD OF THE INVENTION

The present invention relates to novel compounds, which can be used as an intermediates in the process for the preparation of indoline derivative. More specifically the present invention relates to an intermediate compounds, their preparation and use in the process for preparation of Silodosin and its related compounds.

BACKGROUND OF THE INVENTION

Silodosin is an indoline compound, chemically known as 1-(3-Hydroxypropyl)-5-[(2R)-2-({2-[2-(2,2,2-trifluoroethoxy)phenoxy]ethyl}amino)propyl]-2,3-dihydro-1H-indole-7-carboxamide and represented by Formula (I).

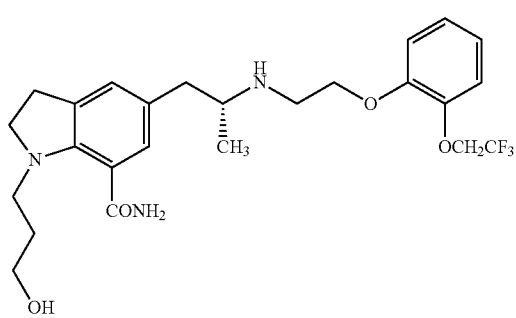

Formula (I)

Silodosin was disclosed in U.S. Pat. No. 5,387,603 as therapeutic agents for the treatment of dysuria, urinary disturbance associated with benign prostatic hyperplasia.

Few processes for the synthesis of Silodosin have been described in the literature.

The Synthesis of Silodosin is relatively complex, involves multiple steps in the preparation of optically active amine compound of Formula (X) and there by condensation with phenoxyethane compound of Formula (Y) followed by deprotection and conversion of cyano group to carbamoyl group.

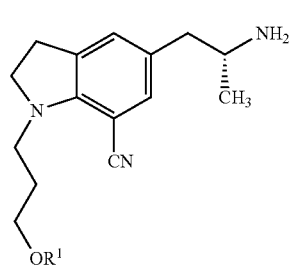

Formula (X)

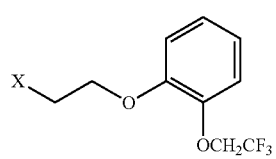

Formula (Y)

EP1806340 patent application relates to a process for the preparation of silodosin comprising mixing 3-{7-cyano-5-[(2R)-2-({2-[2-(2,2,2-trifluoroethoxy)phenoxy]-ethyl}amino)propyl]-2,3-dihydro-1H-indol-1-yl}propyl benzoate of Formula (1) with oxalic acid to produce corresponding monooxalate salt compound. Hydrolyzing the obtained monooxalate compound to yield 1-(3-hydroxypropyl)-5-[(2R)-2-({2-[2-(2,2,2-trifluoroethoxy)phenoxy]-ethyl}amino)propyl]-2,3-dihydro-1H-indole-7-carbonitrile represented by the Formula (2), further hydrolyzing the compound of Formula (2) to yield Silodosin.

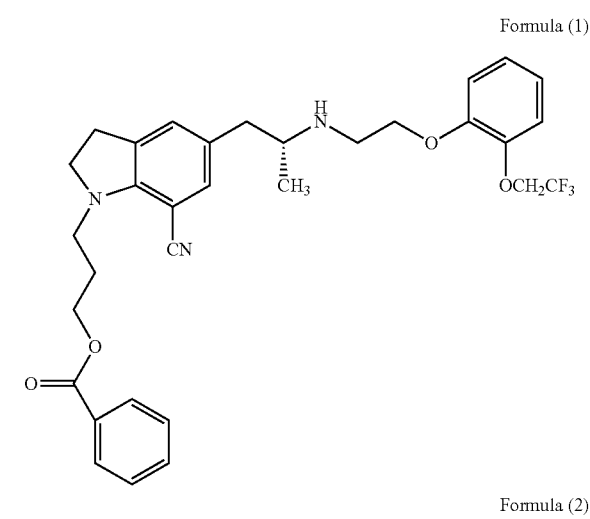

Formula (1)

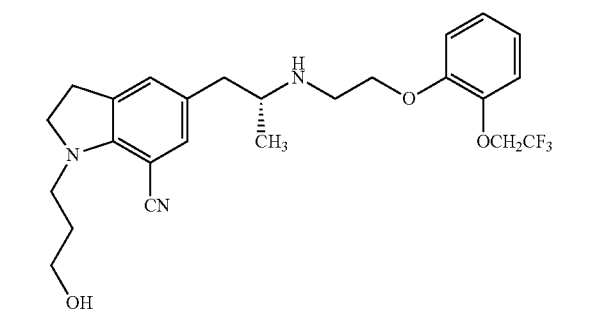

Formula (2)

There are several disadvantages involved in the processes disclosed in prior art references. Mainly, the prior art processes involved alkylation of compound (X) by compound (Y), this reaction often leads to over alkylation and produces undesired compounds accordingly yields of the desired compound are very low. The present inventors have surprisingly found that employing intermediates of the present invention in the process for the preparation of Silodosin, overcomes the drawbacks of the prior art and may be prepared and subsequently converted to Silodosin in high yield and purity.

SUMMARY OF THE INVENTION

According to an aspect of the invention there is provided a process for the synthesis of Silodosin (Compound of Formula I) comprising reductive amination of compound of Formula (VII) and compound of Formula (VIII) in a suitable solvent using a reducing agent.

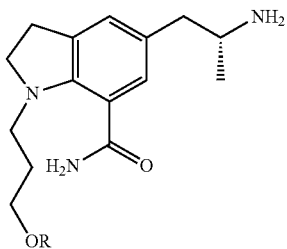

(VII)

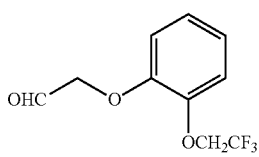

(VIII)

According to another aspect of the invention there is provided a process for the synthesis of Silodosin (Compound of Formula I) comprising reductive amination of compound of Formula (VIII) and compound of Formula (XV) in a suitable solvent using a reducing agent.

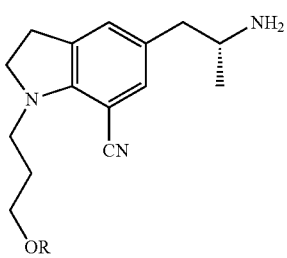

(XV)

According to another aspect of the invention there is provided a compound of formula (VIII) or its pharmaceutically acceptable derivatives thereof.

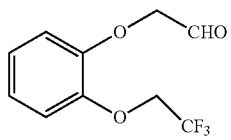

VIII

According to another aspect of the invention there is provided a process for the preparation of compound (VIII) comprising
- (a) Reacting 2,2,2-trifluoroethyl iodide with a solution of 2-methoxy phenol (IX) in the presence of an inorganic base and an organic solvent;
- (b) Stirring the reaction mixture at 90-120° C. for about 8-11 hours;
- (c) Adding water to the reaction mixture of (b) at about 30-45° C.;
- (d) Extracting the reaction mixture of step (c) with an aromatic hydrocarbon solvent followed by separation of aqueous and organic layers;
- (e) Concentrating the organic layer under reduced pressure to get an oil of compound (X);
- (f) Dissolving the oil (compound X) obtained in step (e) in halogenated hydrocarbon solvent followed by addition of boron tribromide at about −10° C. to −25° C.;
- (g) Quenching the reaction mixture of step (f) with aqueous solution of an inorganic base followed by separation of aqueous and organic layers;
- (h) Concentrating the organic layer of step (g) to get a compound (XI) as an oil;
- (i) Dissolving the oily compound (XI) of step (k) in an aprotic polar organic solvent followed by addition of an inorganic base and bromo acetaldehyde ethylene glycol under stirring;
- (j) Stirring the reaction mixture of step (i) at 110-135° C. for 4-6 hours;
- (k) Adding water to the reaction mixture of step (j) at 25-40° C.;
- (l) Adjusting the pH of the reaction mixture of step (k) to 3-4 with mineral acid;
- (m) Extracting the reaction mixture of step (l) with an organic solvent followed by separation of aqueous and organic layers;
- (n) Concentrating the organic layer of step (m) under reduced pressure to get the residue;
- (o) Purifying the residue obtained in step (n) to get the solid compound (XII);
- (p) Dissolving the compound (XII) obtained step (o) in solvent 1,4-dioxane and water followed by the addition of concentrated sulphuric acid;
- (q) Stirring the reaction mixture of step (p) for about 3-6 hours at 85-110° C.;
- (r) Extracting the reaction mixture with an organic solvent followed by separation of aqueous and organic layers;
- (s) Concentrating the organic layer from step (r) under reduced pressure;
- (t) Purifying the residue of step (s) to get the compound (VIII).

According to yet another aspect of the invention there is provided a process for the preparation of compound (VIII) comprises
- a. Reacting compound of formula XI with bromo acetaldehyde ethylene glycol to give compound of formula XII;
- b. Hydrolysing the compound of formula XII to yield compound of Formula VIII wherein compound XI is prepared from catechol.

According to yet another aspect of the invention there is provided a compound of formula XII,

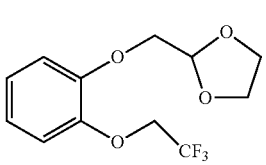

(XII)

According to further aspect of the invention there is provided a process for the preparation of compound (VIII) comprising,
1) Stirring 2-(2,2,2-trifluoroethoxy)phenol(XI), 2-chloroethanol an inorganic base and aprotic polar organic solvent at 90-120° C. for about 8-10 hours;
2) Filtering the reaction mixture of step (1) followed by concentration of the filtrate under reduced pressure to get residue;
3) Extracting the residue of step (2) in to an organic solvent followed by concentration of the organic layer under reduced pressure to get residue;

4) Purifying the residue of step (3) by conventional methods to get a solid compound;
5) Dissolving the solid of step (4) in a halogenated hydrocarbon solvent;
6) Adding to a solution of step (5), oxalyl chloride and halogenated hydrocarbon solvent, followed by triethyl amine at a temperature below −70° C.;
7) Quenching the reaction mixture of step (6) with water and extracting the reaction solution with a halogenated solvent;
8) Concentrating the halogenated solvent under reduced pressure to get a residue;
9) Purifying the residue of step (8) by conventional methods to get the solid compound (VIII).

According to yet another aspect of the invention there is provided a process for the preparation of Silodosin (I) comprising,
 a. Stirring Benzoic acid 3-[5(R)-(2-amino-propyl)-7-cyano-2,3-dihydro-indol-1-yl]-propyl ester (XV), a weak organic acid, an alcohol solvent and a compound, [2-(2,2,2-Trifluoro-ethoxy)-phenoxy]-acetaldehyde (VIII) at 25-40° C. for 1-2 hours.
 b. Adding a reducing agent to the reaction mixture of step a and stirring for about 1-2 hours;
 c. Stirring the reaction mixture of step (b) at a temperature between 35 and 45° C. for about 2-3 hours;
 d. Concentrating the reaction mixture of step (c) by evaporating the solvent under reduced pressure;
 e. Acidifying the residue of step (d) with mineral acid;
 f. Extracting product in ethyl acetate followed by concentration to get the compound of formula (XVI) as an oil;
 g. Adding methanol and aqueous sodium hydroxide solution to an oil of step f and stirring for six hours;
 h. Adding water and extracting the product in an organic solvent;
 i. Concentrating extract of step h to yield a compound of formula (XVII);
 j. Adding DMSO, 5 N sodium hydroxide solution, 30% Hydrogen Peroxide to compound of formula (XVII) followed by stirring at ambient temperature for six to eight hours;
 k. Quenching reaction mixture in sodium sulfite solution;
 l. Extracting product in ethyl acetate followed by acidification with 2N HCl;
 m. Neutralizing aqueous layer with sodium bicarbonate;
 n. Extracting the product in ethyl acetate;
 o. Concentrating the extract of step n under reduced pressure to get the solid residue followed by recrystallization in ethyl acetate to yield Silodosin (I).

According to an aspect of the invention there is provided a process for the preparation of Silodosin (I) comprising,
 a) Stirring Benzoic acid 3-[5(R)-(2-amino-propyl)-7-cyano-2,3-dihydro-indol-1-yl]-propyl ester (XV), DMSO, 30% Hydrogen peroxide and 5N sodium hydroxide solution for 2-4 hrs;
 b) Adding water and extracting the product in an organic solvent;
 c) Concentrate the organic solvent to yield residue;
 d) Adding a weak organic acid, an alcohol solvent and a compound, [2-(2,2,2-Trifluoro-ethoxy)-phenoxy]-acetaldehyde (VIII) to the residue of step (c) at (25-40° and continue stirring for about 1-2 hours; e) Adding a reducing agent to the reaction mixture of step (d) and stirring for about 1-2 hours;
 f) Stirring the reaction mixture of step (e) at a temperature between 35 and 45° C. for about 2-3 hours;
 g) Concentrating the reaction mixture of step (f) by evaporating the solvent under reduced pressure;
 h) Adding aqueous mineral acid to the reaction mixture of step (g);
 i) Extracting the reaction mixture of step (h) into aprotic polar organic solvent;
 j) Concentrating the extraction of step (i) under reduced pressure to get the residue;
 k) Purifying the residue of step (j) by conventional methods;
 l) Dissolving the solid obtained in step (k) in an aprotic polar organic solvent and adding an oxidizing agent followed by inorganic aqueous basic solution;
 m) Stirring the contents of step (l) for about 2-3 hours at about 25-35° C.;
 n) Adding water to the reaction mixture of step (m) and extracting the reaction solution in to an organic solvent;
 o) Concentrating the extractions of step (n) under reduced pressure to get the residue;
 p) Purifying the residue of step (o) by conventional methods to get the compound (I).

According to an aspect of the invention there is provided a process for the preparation of Formula VIII comprising,
 (a) Adding an inorganic base and 2,2,2-trifluoroetthyl iodide to a solution of catechol in an organic solvent;
 (b) Stirring the reaction mixture of step (a) at a temperature 90-130° C. for about 4-8 hours;
 (c) Adding water to the reaction mixture of step (b) at about 30-45° C.;
 (d) Extracting the reaction mixture of step (c) in to an aromatic hydrocarbon solvent followed by separation of aqueous and organic layers;
 (e) Concentrating the organic layer under reduced pressure to get an oil of compound (XI);
 (f) Dissolving the oily compound (XI) of step (e) in an aprotic polar organic solvent followed by addition of an inorganic base and bromo acetaldehyde ethylene glycol under stirring;
 (g) Stirring the reaction mixture of step (f) at about 110-135° C. for about 4-6 hours;
 (h) Adding water to the reaction mixture of step (g) at about 25-40° C.;
 (i) Adjusting the pH of the reaction mixture of step (h) to 3-4 with mineral acid;
 (j) Extracting the reaction mixture of step (i) in to a organic solvent followed by separation of aqueous and organic layers;
 (k) Concentrating the organic solvent of step (j) under reduced pressure to get the residue;
 (l) Purifying the residue obtained in step (k) to get the solid compound (XII);
 (m) Dissolving the compound (XII) obtained step (l) in solvent 1,4-dioxane and water followed by the addition of concentrated sulphuric acid or oxalic acid;
 (n) Stirring the reaction mixture at about 85-110° C. for about 3-6 hours;
 (o) Extracting the reaction mixture with an organic solvent followed by separation of aqueous and organic layers;
 (p) Concentrating the organic solvent from step (o) under reduced pressure;
 (q) Purifying the residue of step (p) to get the compound (VIII).

DETAILED DESCRIPTION OF THE INVENTION

The present invention provides a process for the preparation of Silodosin comprising condensation of compound of formula (VII) and (VIII) via reductive amination using sodiumcyanoborohydride or reduction of in situ formed imine with reducing agents such as sodiumborohydride, sodium triacetoxyborohydride, Raney $N_1$, $H_2$/Pd—C.

An embodiment of the present invention provides a process for the preparation of key intermediate compound (VII) from 7-cyano indoline.

Another embodiment of the present invention provides a process for the preparation of key intermediate compound of Formula (VIII) from 2-methoxy phenol comprising.
(a) addition of an inorganic base and 2,2,2-trifluoroethyl iodide to a solution of 2-methoxy phenol (IX) in an organic solvent;
(b) heating the contents of (a) under stirring to 90-120° C.;
(c) stirring the reaction mixture (b) at a temperature 90-120° C. for about 8-11 hours;
(d) addition of water to the reaction mixture of (c) at about 30-45° C.;
(e) extracting the reaction solution of step (d) in to an aromatic hydrocarbon solvent;
(f) separating the organic layer from the reaction solution of (e);
(g) washing the organic layer with water;
(h) concentrating the organic layer under reduced pressure to get an oil of compound (X);
(i) dissolving the oil (compound X) obtained in step (h) in halogenated hydrocarbon solvent;
(j) addition of boron tribromide to the solution of step (i) at about −10° C.;
(k) stirring the contents of step (j) at about −10° C. to −25° C.;
(l) quenching the reaction mixture of step (k) with aqueous solution of an inorganic base;
(m) separating the organic layer from the reaction solution of step (l) and washing with water;
(n) concentrating the organic solvent of step (m) to get a compound (XI) as an oil;
(o) dissolving the oily compound (XI) of step (n) in an aprotic polar organic solvent;
(p) addition of an inorganic base and bromo acetaldehyde ethylene glycol to the solution of step (o) under stirring;
(q) stirring the reaction mixture of step (p) at about 110-135° C. for about 4-6 hours;
(r) addition of water to the reaction mixture of step (q) at a temperature between about 25 and 40° C.;
(s) adjusting the pH of the reaction solution of step (r) to 3-4 with mineral acid;
(t) extracting the reaction solution of step (s) in to a organic solvent;
(u) separating the organic layer from the extraction of step (t) and washing with water;
(v) concentrating the organic solvent of step (u) under reduced pressure to get the residue;
(w) purifying the residue obtained in step (v) to get the solid compound (XII);
(x) dissolving the compound (XII) obtained step (w) in solvent 1,4-dioxane and water;
(y) addition of concentrated sulphuric acid or oxalic acid to the reaction solution of step (x) and stirring the contents for about 3-6 hours at about 85-110° C.;
(z) diluting the reaction mixture of step (y) with water and extracting the reaction solution with an organic solvent;
(aa) separating the organic layer form the extractions of step (z) and washing with water;
(bb) concentrating the organic solvent from step (aa) under reduced pressure and
(cc) purifying the residue of step (bb) to get the compound (VIII).

In another embodiment of the present invention provides a process for the preparation of key intermediate of compound of Formula (VIII) from catechol comprising.
(a) addition of an inorganic base and 2,2,2-trifluoroetthyl iodide to a solution of catechol in an organic solvent;
(b) heating the contents of (a) under stirring to 90-130° C.;
(c) stirring the reaction mixture (b) at a temperature 90-130° C. for about 4-8 hours;
(d) addition of water to the reaction mixture of (c) at about 30-45° C.;
(e) extracting the reaction solution of step (d) in to an aromatic hydrocarbon solvent;
(f) separating the organic layer from the reaction solution of (e);
(g) washing the organic layer with water;
(h) concentrating the organic layer under reduced pressure to get an oil of compound (XI);
(i) dissolving the oily compound (XI) of step (h) in an aprotic polar organic solvent;
(j) addition of an inorganic base and bromo acetaldehyde ethylene glycol to the solution of step (i) under stirring;
(k) stirring the reaction mixture of step (j) at about 110-135° C. for about 4-6 hours;
(l) addition of water to the reaction mixture of step (k) at a temperature between about 25 and 40° C.;
(m) adjusting the pH of the reaction solution of step (l) to 3-4 with mineral acid;
(n) extracting the reaction solution of step (m) in to a organic solvent;
(o) separating the organic layer from the extraction of step (n) and washing with water;
(p) concentrating the organic solvent of step (o) under reduced pressure to get the residue;
(q) purifying the residue obtained in step (p) to get the solid compound (XII);
(r) dissolving the compound (XII) obtained step (q) in solvent 1,4-dioxane and water;
(s) addition of concentrated sulphuric acid or oxalic acid to the reaction solution of step (r) and stirring the contents for about 3-6 hours at about 85-110° C.;
(t) diluting the reaction mixture of step(s) with water and extracting the reaction solution with an organic solvent;
(u) separating the organic layer form the extractions of step (t) and washing with water;
(v) concentrating the organic solvent from step (u) under reduced pressure
(w) purifying the residue of step (v) to get the compound (VIII).

An inorganic base used in the reaction selected form the group but not limited to alkali metal hydroxide, alkali metal cabonate and alkali metal bicarbonate. Preferably the inorganic base is alkali metal cabonate and potassium carbonate is especially preferable. The halogenated hydrocarbon solvent used in the above reaction is selected from the group consisting methylene chloride, chloroform, carbon tetrachloride, ethylene dichloride and the like. The aprotic polar solvent used in the above reaction is selected from the group containing dimethyl formamide, N-methylpyrrolidone, acetonitrile, dimethyl sulfoxide and the like.

Purification technique used for isolation of the solid from the residue obtained in above reactions comprises column chromatography, recrystallization and the like.

Alternatively the compound (VIII) can also be obtained from a compound 2-(2,2,2-trifluoroethoxy)phenol (XI) by the process comprising,
1) stirring the contents of 2-(2,2,2-trifluoroethoxy)phenol (XI), 2-chloroethanol an inorganic base and aprotic polar organic solvent at about 90-120° C. for about 8-10 hours;
2) filtration of the reaction mixture of step (1) and concentrating the filtrate under reduced pressure to get residue;
3) extracting the residue of step (2) in to an organic solvent
4) concentrating the organic extract obtained in step (3) under reduced pressure to get residue;
5) purifying the residue of step (4) by conventional methods to get a solid compound;

6) dissolving the solid of step (5) in a halogenated hydrocarbon solvent and adding to a solution of oxalyl chloride and halogenated hydrocarbon solvent, followed by triethyl amine at a temperature below −70° C.;

7) quenching the reaction mixture of step (4) with water and extracting the reaction solution with a halogenated solvent;

8) washing the organic extractions of step (5) with water and concentrating the solvent under reduced pressure to get a residue and 9) purifying the residue of step (6) by conventional methods to get the solid compound (VIII).

An inorganic base used in the above reaction selected form the group but not limited to alkali metal hydroxide, alkali metal cabonate and alkali metal bicarbonate. Preferably the inorganic base is alkali metal cabonate and potassium carbonate is especially preferable. The aprotic polar solvent used in the above reaction is selected from the group consisting dimethyl formamide, N-methylpyrrolidone, acetonitrile, dimethyl sulfoxide and the like. The halogenated hydrocarbon solvent used in the above reaction is selected from the group containing methylene chloride, chloroform, carbon tetrachloride, ethylene dichloride and the like.

Purification technique used for isolation of the solid from the residue obtained in above reactions comprises column chromatography, recrystallization and the like.

In an embodiment of the present invention provides a novel process for the preparation of silodosin (I) comprising, a. stirring the contents of a compound, Benzoic acid 3-[5 (R)-(2-amino-propyl)-7-cyano-2,3-dihydro-indol-1-yl]-propyl ester (XV), DMSO, 30% Hydrogen peroxide and 5N NaOH solution for 2-4 hrs;

b. add water and extract product in an organic solvent;

c. concentrate to yield residue;

d. add a weak organic acid, an alcohol solvent and a compound, [2-(2,2,2-Trifluoro-ethoxy)-phenoxy]-acetaldehyde (VIII) to the residue of step c at ambient temperature)(25-40° and continue stirring for about 1-2 hours;

e. addition of a reducing agent to the reaction mixture of step d and stirring for about 1-2 hours;

f. stirring the reaction mixture of step e at a temperature between 35 and 45° C. for about 2-3 hours;

g. concentrating the reaction mixture of step f by evaporating the solvent under reduced pressure;

h. addition of aqueous mineral acid to the reaction mixture of step g;

i. extracting the reaction mixture of step h into an organic solvent;

j. concentrating the extractions of step i under reduced pressure to get the residue;

k. purifying the residue of step j by conventional methods;

l. dissolving the solid obtained in step k in an aprotic polar organic solvent and adding an oxidizing agent followed by inorganic aqueous basic solution;

m. stirring the contents of step 1 for about 2-3 hours at about 25-35° C.;

n. addition of water to the reaction mixture of step m and extracting the reaction solution in to an organic solvent;

o. concentrating the extractions of step n under reduced pressure to get the residue and p. purifying the residue of step o by conventional methods to get the compound (I).

The weak organic base used in the above reaction selected form the group but not limited to acetic acid, trifluoro acetic acid, formic acid. An alcohol solvent used in the above reaction is selected from the group consisting lower alcohol solvent like methanol, ethanol, propanol, isopropanol, and tertiary butanol. The reducing agent used in the above reaction is selected from the group consisting alkaliborohydride, alkali cyanoborohydride, ranynickel, and Palladium on carbon, preferably alkali cyanoborohydride most preferably sodium-cyanoboro hydride. The aprotic polar solvent used in the above reaction is selected from the group consisting dimethyl formamide, N-methylpyrrolidone, acetonitrile, dimethly sulfoxide and the like. The oxidizing agent used in the above reaction is hydrogen peroxide.

Purification technique used for isolation of the solid from the residue obtained in above reactions comprises column chromatography, recrystallization and the like.

In an embodiment of the present invention provide a process for the preparation of key intermediate compound of formula (VIII) from 2-(2,2,2-trifluoroethoxy)phenol (XI).

In another embodiment of the present invention provide novel sub-intermediate compounds used in the preparation of key intermediate compounds (VII) and (VIII).

In yet another embodiment of the present invention provides a process for the preparation of compound (VII) comprising the steps for the preparation of compounds (II), (IV), (V), (VI) and conversion to compound (VIII).

The first embodiment of the present invention which provides a process for preparing compound (VII) from 7-Cyano indoline comprising steps, which can be shown by Scheme-1.

Scheme 1

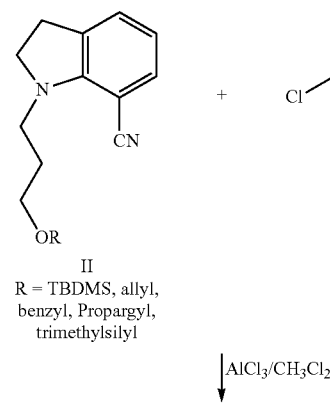

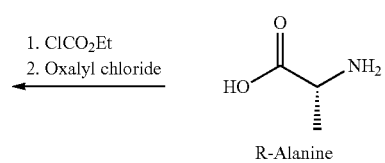

-continued

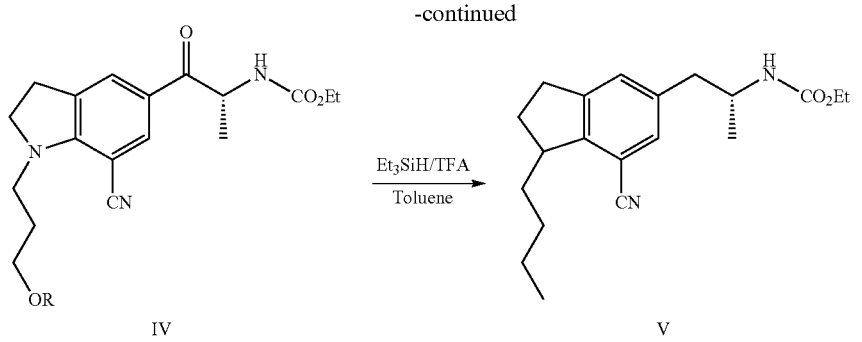

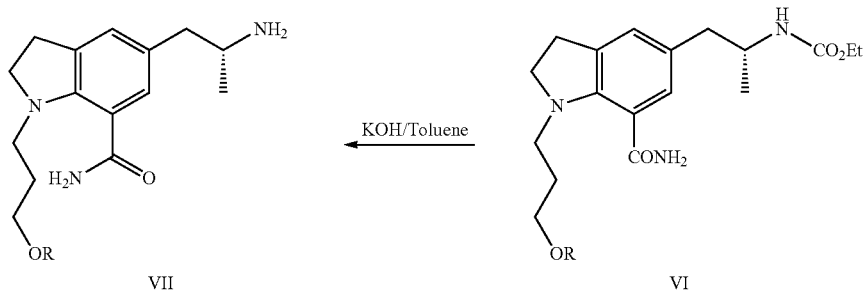

In an embodiment of the present invention provide a process for the preparation of compound (VIII) comprises reaction of compound of formula XI with bromo acetaldehyde ethylene glycol to give compound of formula XII; followed by the hydrolysis of compound of formula XII to yield compound of Formula VIII, wherein compound XI is prepared from catechol In another embodiment of the present invention provides a process for the preparation of compound of formula (VIII) from 2-methoxy phenol (compound IX).

In yet another embodiment of the present invention process for the preparation of compound (VIII) from Catechol.

In an embodiment of the present invention provides process for the preparation of compound (VIII) from 2-methoxy phenol (compound of formula IX) comprising the steps for the preparation of compounds (X), (XI) and (XII).

The process for the preparation of compound (VIII) can be shown as below Scheme-2.

Scheme 2

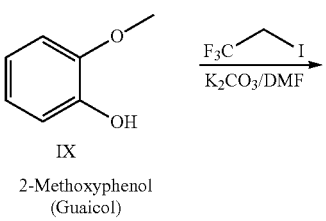

2-Methoxyphenol
(Guaicol)

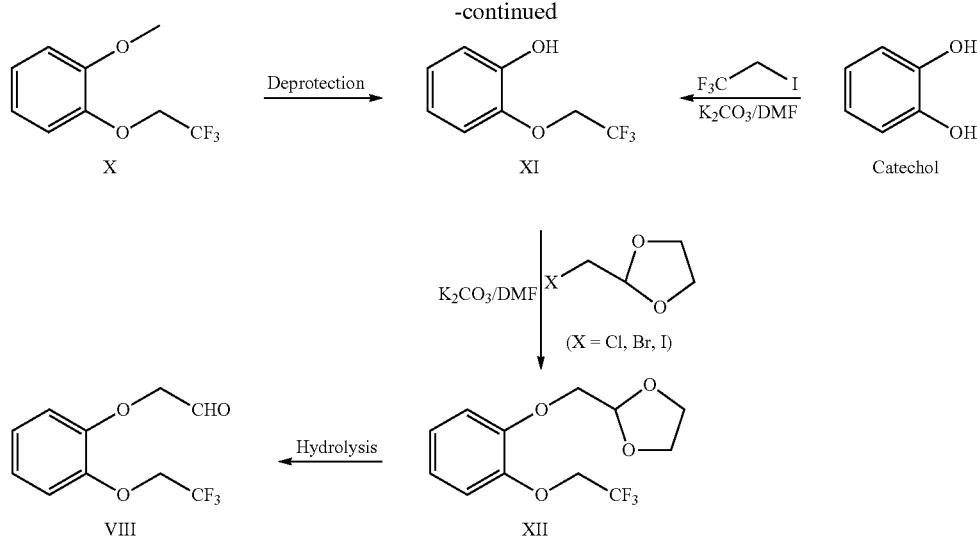

In an embodiment of the present invention provide a novel intermediate of formula XII.

In an embodiment of the present invention provide a process for the preparation of key intermediate compound (VIII) from 2-trifluoromethoxy phenol of compound (XI).

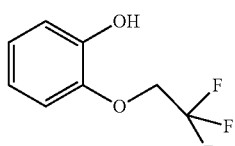
XI

The process for the preparation of compound of formula VIII from 2-trifluoromethoxy phenol (compound of formula XI) can be shown as below Scheme-3.

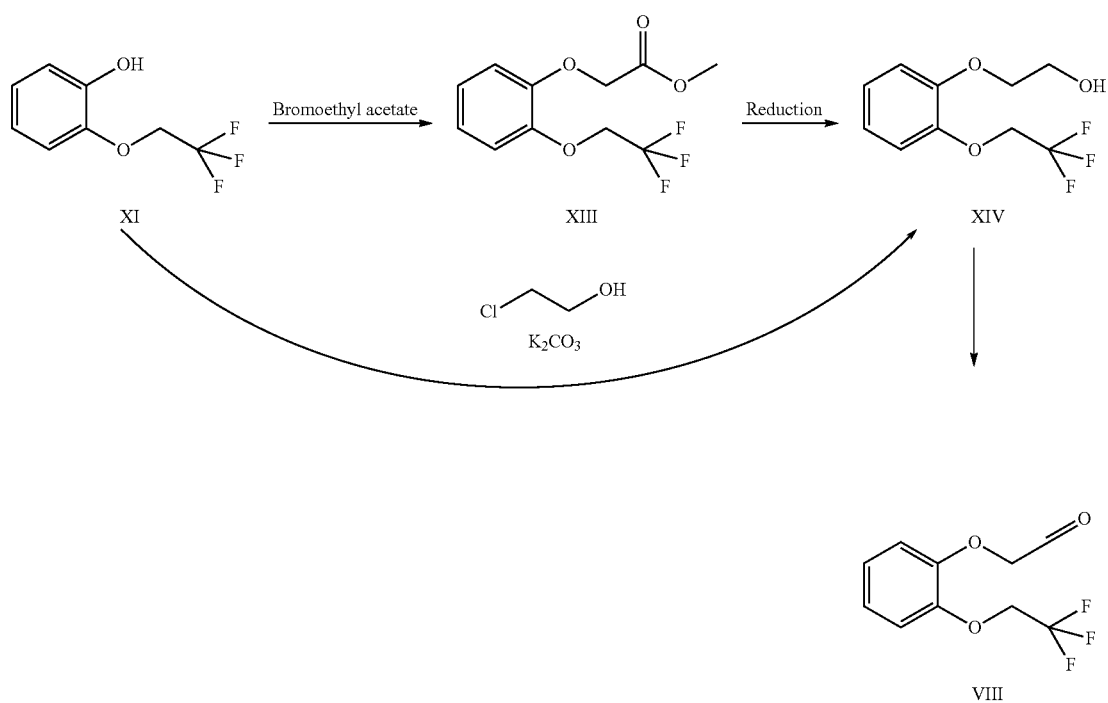

In yet another embodiment of the present invention provides a process for the preparation of compound of formula (I) comprising condensation of compound (VII) and (VIII) by reductive amination in a suitable solvent without isolating the Schiff-base compound.

The process for the preparation of compound of Formula I by reductive amination of compound (VII) and (VIII) followed by deprotection can be shown as below Scheme-4.

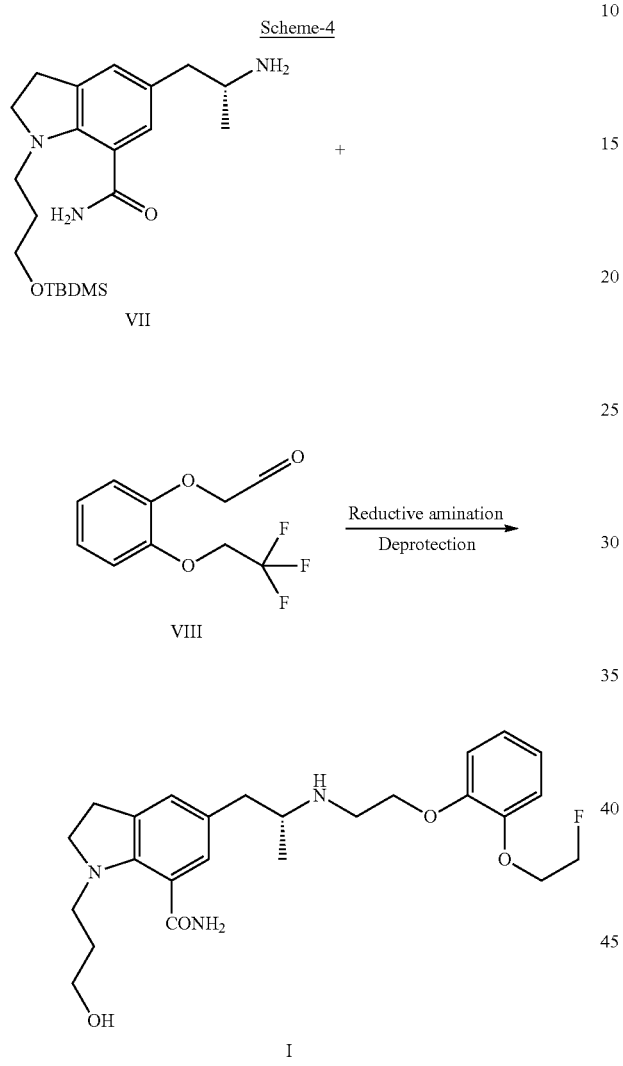

The process of reductive amination as shown in above Scheme-4 comprising addition of a compound (VIII) to a solution of compound (VII) in an organic solvent. Stirring the contents in the presence of a acid and further reacting with a reducing agent followed by isolation of the obtained by product by common procedures too yield compound (I).

Another embodiment of the invention is process for the preparation of Silodosin (compound of Formula I) comprising condensation of novel intermediate compound (VIII) and compound (XV) followed by deprotection and oxidation.

The process for the preparation of Silodosin (compound of Formula I) comprising steps, (a) stirring a Benzoic acid 3-[5(R)-(2-amino-propyl)-7-cyano-2,3-dihydro-indol-1-yl]-propyl ester (XV), a weak organic acid, an alcohol solvent and a compound, [2-(2,2,2-Trifluoro-ethoxy)-phenoxy]-acetaldehyde (VIII) at ambient temperature and continue stirring for about 1-2 hour at 25-40° C.

(b) addition of a reducing agent to the reaction mixture of step a and stirring for about 1-2 hours;

(c) stirring the reaction mixture of step b at a temperature between 35 and 45° C. for about 2-3 hours;

(d) concentrating the reaction mixture of step f by evaporating the solvent under reduced pressure;

(e) acidify the residue of step d with mineral acid and extract product in ethyl acetate (f) concentrate the extract of step e to get the compound of formula (XVI) as an oil (g) add methanol, aqueous solution of NaOH to an oil of step f and continue stirring for six hrs.;

(h) add water and extract product in an organic solvent (i) concentrate extract of step h to yield a compound of formula (XVII)

(j) add DMSO, 5 N NaOH solution, 30% Hydrogen Peroxide to compound of formula (XVII) and Stirr at ambient temperature for six to eight hrs;

(k) quench reaction mixture in sodium sulfite solution;

(l) extract product in ethyl acetate and acidify with 2N HCl (m) neutralize aqueous layer with sodium bicarbonate (n) extract product in ethyl acetate (o) concentrating the extract of step n under reduced pressure to get the solid residue and recrystallized from ethyl acetate to yield Silodosin (I).

The process for the preparation of Silodosin (I) by condensation of compound (VIII) and compound (XV) can be shown as below Scheme-5.

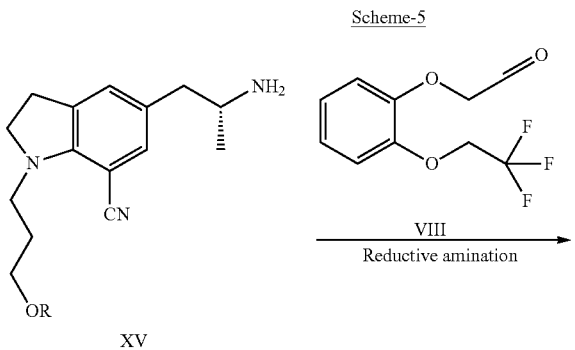

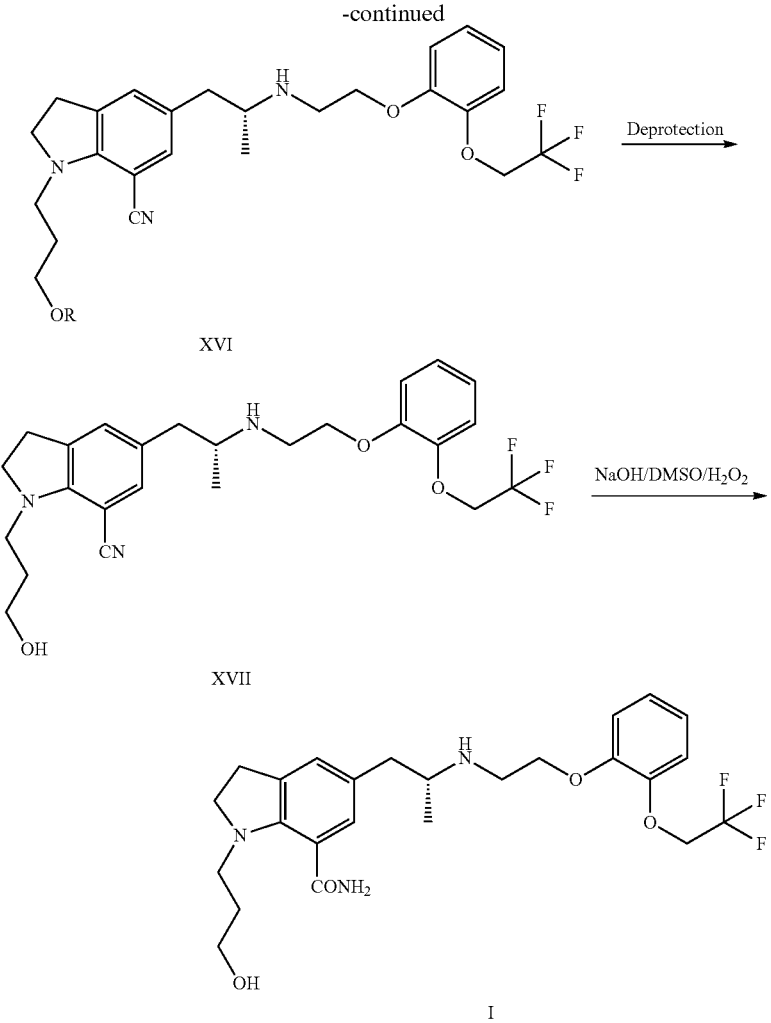

The present invention further illustrated in detail by the below examples which are however not limit to the scope of the invention.

EXAMPLES

Reference Example 1

Preparation of 1-[3-(t-Butyl-dimethyl-silanyloxy)-propyl]-2,3-dihydro-1H-indole-7-carbonitrile (II)

A mixture of 7-Cyano indoline (5 g, 0.035 mole), dimethyl formamide (50 ml) and powdered $K_2CO_3$ (9.6 g, 0.07 mole) was heated to 70° C. and Toluene-4-sulfonic acid-3-(t-butyl dimethyl)-silanyloxypropyl ester (12.7 g 0.037 mole) was added to reaction mixture. Reaction mixture was quenched in distilled water and product extracted in ethyl acetate and extract washed with saturated brine solution, dried over anhydrous sodium sulphate. The solvent was evaporated under reduced pressure to give 10 g of (II) as oil.

Reference Example 2

Preparation of R—(N-Ethoxy carbonyl) alanine (III)

R-Alanine (4.45 g, 0.05 moles) was dissolved in 50 ml 1 N sodium hydroxide solution and cooled to 15° C. Ethyl chloroformate (5 ml, 0.05 mole) was added while maintaining the pH of reaction mixture at 9-9.5 by using 1N sodium hydroxide solution. Reaction mixture was cooled to 0-5° C. and extracted with diethyl ether. Orthophosphoric acid was added to aqueous layer and pH was adjusted below 1.0. Product was extracted in dichloromethane. Organic layer was dried over sodium sulphate. The solvent was evaporated under reduced to give 6.5 g of R—(N-Ethoxy carbonyl)alanine as oil.

Example-1

Preparation of (2-{1-[3-(tert-Butyl-dimethyl-silanyloxy)-propyl]-7-cyano-2,3-dihydro-1H-indol-5-yl}-1-methyl-2-oxo-ethyl)-carbamic acid ethyl ester, (IV)

To the solution of R—(N-Ethoxy carbonyl)alanine (III) (16.1 g, 0.1 moles) in dry dichloromethane (300 ml) at 0° C. under inert atmosphere was added 0.5 ml DMF and oxalyl chloride (10 ml, 0.0105 mole). Reaction mixture was allowed to warm to room temperature with stirring and after 2 hours it was cooled to −15° C. Then $AlCl_3$ (28.4 g, 0.21 mole) was added in one portion. To the reaction mixture a solution of 1-[3-(tert-Butyl-dimethyl-silanyloxy)-propyl]-2,3-dihydro-1H-indole-7-carbonitrile (II) (31.65 g, 0.1 mole) in 150 ml dichloromethane was added at −15. Reaction mixture was quenched with 150 ml of cold water and 50 ml of 1N HCl.

Organic layer was washed with saturated brine solution and dried over anhydrous sodium sulphate. The solvent was evaporated under reduced to give 30 g of compound (IV) as oil.

Example-2

Preparation of (2-{1-[3-(tert-Butyl-dimethyl-silanyloxy)-propyl]-7-cyano-2,3-dihydro-1H-indol-5-yl}-1-methyl-ethyl)-carbamic acid ethyl ester (V)

A mixture of (2-{1-[3-(tert-Butyl-dimethyl-silanyloxy)-propyl]-7-cyano-2,3-dihydro-1H-indol-5-yl}-1-methyl-2-oxo-ethyl)-carbamic acid ethyl ester (IV) (10 g, 0.02 mole), toluene (80 ml), triethyl silyl hydride (5.57 g, 0.04 mol) and trifluoroacetic acid (1.36 g, 0.01 mole), was stirred at 25-30° C. for a period of 6 hours. The reaction mass was quenched with water (50 ml) and toluene layer was dried over sodium sulphate. The solvent was evaporated under reduced to give 6.7 g of (V) as oil.

Example-3

Preparation of (2-{1-[3-(tert-Butyl-dimethyl-silanyloxy)-propyl]-7-carbamoyl-2,3-dihydro-1H-indol-5-yl}-1-methyl-ethyl)-carbamic acid ethyl ester (VI)

To a solution of (2-{1-[3-(tert-Butyl-dimethyl-silanyloxy)-propyl]-7-cyano-2,3-dihydro-1H-indol-5-yl}-1-methyl-ethyl)-carbamic acid ethyl ester compound (V) (6 g, 0.01 mole) in DMSO (100 ml) was added 30% $H_2O_2$ (15 ml) and the mixture was stirred at 25-30° C. for 15 min. To the reaction mixture was then added 5 N NaOH solution (15 ml) and the mixture was stirred at above temperature for further period of 3 h. Acetic acid (18 ml) was added and reaction mixture was diluted with water. The mixture was extracted with ethyl acetate. The organic layer was dried over sodium sulphate and the solvent was evaporated under reduced pressure to give 3.68 g of (VI) as pale yellow waxy solid.

Example-4

Preparation of 5-(2-Amino-propyl)-1-[3-(tert-butyl-dimethyl-silanyloxy)-propyl]-2,3-dihydro-1H-indole-7-carboxylic acid amide (VII)

(2-{1-[3-(tert-Butyl-dimethyl-silanyloxy)-propyl]-7-carbamoyl-2,3-dihydro-1H-indol-5-yl}-1-methyl-ethyl)-carbamic acid ethyl ester (VI), (3 g, 0.006 mole) was heated to reflux in toluene (25 ml) with KOH (2 g:0.03 mole) for 3 h. Reaction mixture was quenched with water and toluene layer was separated and washed with water. The organic layer was dried over sodium sulphate. The solvent was evaporated under reduced to give 1.84 g of (VII) as brown oily mass.

Example-5

Preparation of 1-Methoxy-2-(2,2,2-trifluoroethoxy)benzene (X)

To a solution of 2-Methoxy phenol (IX) (5 g, 0.04 moles) in N-methylpyrrolidone (50 ml) were added, potassium carbonate (7.8 g, 0.06 mole) and 2,2,2-trifluoroethyl iodide (33.8 g, 0.16 mole) under stirring. The reaction mixture was stirred vigorously at 120° C. for 10 hours. Water (150 ml) was added to the reaction mixture and the mixture was extracted in Toluene (250 ml). Organic layer was washed with 1 N Sodium hydroxide solution (150 ml), followed by brine wash. The extract was dried over sodium sulphate. The solvent was evaporated under reduced pressure to give 7.2 g of (X) as oil. Purity (by GC)=94%

Example-6

Preparation of 2-(2,2,2-trifluoroethoxy)phenol (XI)

Boron tribromide (2.8 ml, 0.03 mole) was added to a solution of 1-methoxy-2-(2,2,2-trifluoroethoxy)benzene (X) (6.0 g, 0.03 mole) in methylene chloride (90 ml) with stirring below −10° C. Reaction was stirred at −10 to −20° C. for 30 minutes. The reaction mixture was quenched using aqueous sodium bicarbonate solution. Organic layer was separated, washed with water and dried over sodium sulphate. The solvent was evaporated under reduced pressure to give 4.0 g of (XI) as oil. Purity (by GC)=95%.

Example-7

Preparation of 2-(2,2,2-trifluoroethoxy)phenol (XI)

To a solution of catechol (5 g, 0.045 moles) in dimethylsulfoxide (25 ml) were added, potassium carbonate (12.55 g, 0.09 mole) and 2,2,2-trifluoroethyl iodide (4.77 g, 0.023 mole) under stirring. The reaction mixture was stirred vigorously at 120° C. for 6 hours. Water (150 ml) was added to the reaction mixture and the mixture was extracted in Toluene (250 ml). Organic layer was washed with 1 N Sodium hydroxide solution (150 ml), followed by brine wash. The extract was dried over sodium sulphate. The solvent was evaporated under reduced pressure to give 4.0 g of (XI) as oil. Purity (by GC)=96%

Example-8

Preparation of 2-[2-(2,2,2-trifluoro ethoxy)phenoxy 3]dioxalane (XII)

Mixture of 2-(2,2,2-trifluoroethoxy)phenol (XI) (6 g, 0.031 mole), N-methyl-2-pyrrolidone (30 ml), potassium carbonate (8.6 g 0.062 mole) and Bromo acetaldehyde ethylene glycol (6.26 g, 0.037 mole) was heated to 115-120° C. and stirred for 5 hours. Water (120 ml) was added to reaction mixture at ambient temperature and pH adjusted to 3-4 with mineral acid. The mixture was extracted using Ethyl acetate (200 ml). Organic layer was washed with aqueous sodium bicarbonate solution followed by water. Organic layer was dried over sodium sulphate. The solvent was evaporated under reduced pressure and the residue was purified by column chromatography on silica gel using a mixture of ethyl acetate and hexane (5/95) as eluent to give 4.0 g of (XII) as colourless solid, melting at 37.6-39.6° C.
Purity (By GC)=98%

IR (Mk): 1748.8, 1598.6, 1509, 1451.5, 1261.1, 1163, 1127.2, 1055.9, 1047.1 cm$^{-1}$ $^1$H NMR (300 MHz, CDCl$_3$): 3.93-3.98 (2H, d), 4.05-4.08 (4H, m), 4.36-4.45 (2H, q), 5.314-5.338 (1H, t), 6.90-7.05 (4H, m), ppm $^{13}$C NMR (75 MHz, CDCl$_3$): 65.36 (2C), 67.39-68.79 (1C), 70.01 (1C), 101.89 (1C), 114.8, 118.10, 121.87, 124.18 (4C), 149.62 (1C), 147.48 (1C), 128.22-129.03 (1C)

Example-9

Preparation of [2-(2,2,2-Trifluoro-ethoxy)-phenoxy]-acetaldehyde (VIII)

To a solution of 2-[2-(2,2,2-trifluoro ethoxy)phenoxy ethyl]-[1,3]dioxalane (VII) (6 g, 0.022 mole) in 1,4-Dioxane (12 ml) and water (50 ml) was added concentrated Sulphuric acid (4.6 ml, 0.086 mole). Reaction mixture was heated to 95-100° C. and stirred for 5 hours and cooled to ambient temperature. To the reaction mixture was added water (30 ml) and extracted the mixture in ethyl acetate (100 ml). Organic layer was washed with water and dried over sodium sulphate. The solvent was evaporated under reduced pressure and the residue was purified by column chromatography on silica gel using a mixture of ethyl acetate and hexane (5/95) as eluent to give 3.0 g of (VIII) as colourless solid, melting at 55.3-57.5° C.
Purity (By GC)=98%

IR (KBr)=1739.4, 1596.5, 1509.6, 1457, 1258.4, 1158.2, 1127.7, 1114.7, 1029, 978.0, 964.7, 919.1, 736.3 cm$^{-1}$ $^1$H NMR (300 MHz, CDCl$_3$)=4.47-4.36 (2H, q), 4.62 (2H, s), 6.86-7.06 (4H, m), 9.86 (1H, s) ppm.

$^{13}$C NMR (75 MHz, CDCl$_3$)=67.03-68.43 (1C), 74.13 (1C), 115.61, 117.42, 122.95, 123.99 (4C), 124.13-125.23 (1C), 147.62 (1C), 148.45 (1C), 199.0 (1C) ppm

Example-10

Preparation of 2-[2-(2,2,2-Trifluoro-ethoxy)-phenoxy]-ethanol (XIV)

To a mixture of 2-(2,2,2-trifluoroethoxy)phenol (XI) (6 g, 0.03 mole), N,N-dimethylformamide (50 ml) and potassium carbonate (13.0 g, 0.09 mole) was added 2-chloroethanol (4.2 ml, 0.06 mole). Reaction mixture was heated to 100-105° C. and stirred for 10 hours. Reaction mass was filtered and the filtrate was concentrated under reduced pressure to distill out the N,N-Dimethyl formamide. To the residue was added water and product was extracted in ethyl acetate (50 ml). The organic layer was washed with water and dried over sodium sulphate. The solvent was evaporated under reduced pressure and the residue was purified by column chromatography on silica gel using a mixture of ethyl acetate and hexane (5/95) as eluent to give 4.0 g of (XIV) as oil. Purity (By GC)=95%

Example-11

Preparation of [2-(2,2,2-Trifluoro-ethoxy)-phenoxy]-acetaldehyde (VIII)

A solution of oxalyl chloride (0.73 ml, 8 mmole) in Dichloromethane (7 ml) was cooled below −70° C. Then charged DMSO (1.2 ml) below −70° C. To the reaction mixture was added, solution of 2-[2-(2,2,2-Trifluoro-ethoxy)-phenoxy]-ethanol (XIV) (1.0 g, 4 mmole) in Dichloromethane (10 ml) over a period of 10 minutes below −50° C. Triethylamine (2.3 ml, 0.016 mole) was added below −70° C. Reaction mixture was quenched in cold water and the product was extracted with Dichloromethane (10 ml). Organic layer was washed with aqueous sodium bicarbonate solution followed by washing with water. Dried the organic layer over sodium sulphate. The solvent was evaporated under reduced pressure and the residue was purified by column chromatography on silica gel using a mixture of ethyl acetate and hexane (5/95) as eluent to give 0.6 g of (VIII) as colourless solid, melting at 57-58° C.
Purity (By GC)=98%

The physical properties of this compound were identical to those of the compound prepared in reference example 9

Example-12

Preparation of [2-(2,2,2-Trifluoro-ethoxy)-phenoxy]-acetaldehyde (VIII)

2-[2-(2,2,2-Trifluoro-ethoxy)-phenoxy]-ethanol (XIV) (6 g, 0.025 moles) was added to dichloromethane (60 ml). To this solution sodium bicarbonate (1.2 g, in 10 ml water) was added. Reaction mixture was cooled to 0° C. and potassium bromide (0.24 g in 1 ml of water) and TEMPO (2,2,6,6-Tetramethylpiperidine-1-oxyl) (0.02 g, 0.13 mmole) were added in single lot. To this reaction mixture sodium hypochlorite solution (45 ml of 12.5% w/v) was added over a period of 15 minutes at 0-5° C. Continued stirring of reaction mass at 0-5°. After completion of reaction, organic layer was separated. The aqueous layer was extracted with dichloromethane. Combined organic layer was washed with 10% aqueous sodium hydroxide solution, followed by brine. The organic layer was dried over sodium sulphate. The solvent was evaporated under reduced pressure and the residue was purified by column chromatography on silica gel using a mixture of ethyl acetate and hexane (5/95) as eluent to give 0.40 g of (VIII) as colourless solid, melting at 57-58° C.
Purity (By GC)=98%

The physical properties of this compound were identical to those of the compound prepared in reference example 9.

Example-13

Preparation of Benzoic acid-3-[7-cyano-5(R)-(2-{2-[2-(2,2,2-trifluoro-ethoxy)-phenoxy]-ethylamino}-propyl)-2,3-dihydro-indol-1-yl]-propyl ester (XVI)

A mixture of Benzoic acid 3-[5(R)-(2-amino-propyl)-7-cyano-2,3-dihydro-indol-1-yl]-propyl ester (XV) (10 g, 0.027 mole), methanol (50 ml), glacial acetic acid (0.5 g, 8 mmole) and [2-(2,2,2-Trifluoro-ethoxy)-phenoxy]-acetaldehyde (VIII) (7.6 g, 0.032 mole) was stirred at ambient temperature for 1 hour. To this sodium cyanoborohydride (2.14 g, 0.04 mole) was added and continued stirring at 25-30° c. for 1 hour. Reaction mass was then heated to 40-45° C. and stirred for 2 hours. After the completion of reaction solvent, was evaporated under reduced pressure and water was added to the residue. Reaction mass was acidified with aqueous mineral acid and extracted the mixture in ethyl acetate. Organic layer was washed with water and dried over sodium sulphate. The solvent was evaporated under reduced pressure and the residue was purified by column chromatography on silica gel using a mixture of ethyl acetate and hexane (5/95) as eluent to give 9.6 g of (XVI) as oil.
Purity (By HPLC)=98%

Example-14

Preparation of Preparation of 1-(3-Hydroxy-propyl)-5-(2(R)-{2-[2-(2,2,2-trifluoro-ethoxy)-phenoxy]-ethylamino}-propyl)-2,3-dihydro-1H-indol-7-carboxylic acid amide (I)(Silodosin)

To a solution of Benzoic acid 3-[5(R)-(2-amino-propyl)-7-cyano-2,3-dihydro-indol-1-yl]-propyl ester (XV) (3.5 g, 10 mmole) in Dimethyl sulphoxide (60 ml), charged Hydrogen peroxide (10% w/w) (11 ml). Then added 5 N sodium hydroxide solution (12.3 ml) and reaction mass was stirred for 2 hours. After completion of reaction water was added and extracted the product in ethyl acetate. Organic layer was washed with brine and dried over sodium sulphate. The solvent was evaporated below 40° C. under reduced pressure and added methanol (25 ml). To this solution charged glacial acetic acid (0.25 g, 4 mmole) and [2-(2,2,2-Trifluoro-ethoxy)-phenoxy]-acetaldehyde (VIII) (3 g, 0.0125 mole). Reaction mixture was stirred at 25-30° C. for 1 hour. Then reacted with sodium cyanoborohydride (0.15 g, 2.8 mmoles) and heated at 40-45° C. for 2 hours. After the completion of reaction solvent was distilled off below 40° C. under reduced pressure and added water to the residue. Reaction mass was then acidified with aqueous mineral acid. The aqueous layer was then basified and product was extracted in ethyl acetate. Organic layer was washed with water and dried over sodium sulphate. The solvent was evaporated under reduced pressure and the residue was purified by column chromatography on silica gel using a mixture of ethyl acetate and hexane (5/95) as eluent to give 0.8 g of (I) as yellow solid. Purity (by HPLC)= 98%

Example 15

Preparation of 1-(3-hydroxypropyl)-5-[(2R)-({2-[2-(2,2,2-trifluoroethoxy)phenoxy]-ethyl}amino) propyl]-2,3-dihydro-1H-indole-7-carbonitrile (XVII)

A mixture of 3-[7-Cyano-5(R)-[-2-{2-[2-(2,2,2-trifluoro-ethoxy)-phenoxy]ethyl}amino) propyl]-2,3-dihydro-1H-indol-1-yl}propyl benzoate (XVI) (6.0 g, 0.010 mole), methanol (30 ml) and aqueous solution of Sodium hydroxide (1.6 g in 8 ml of water) was stirred at ambient temperature for 6 hours. To the reaction mixture water (90 ml) was added and product was extracted with ethyl acetate (90 ml). The organic layer was washed with saturated sodium bicarbonate solution followed by brine wash and dried over anhydrous sodium sulfate. The solvent was evaporated under reduced pressure to give 3.85 g of (XVII).

Example 16

Preparation of 1-(3-Hydroxy-propyl)-5(R)-(2-{2-[2-(2,2,2-trifluoro-ethoxy)-phenoxy]-ethylamino}-propyl)-2,3-dihydro-1H-indol-7-carboxylic acid amide (I) (Silodosin)

To a solution of 1-(3-hydroxypropyl)-5(R)-[2-({2-[2-(2,2,2-trifluoroethoxy)phenoxy]-ethyl}amino)propyl]-2,3-dihydro-1H-indole-7-carbonitrile (XVII) (6.0 g, 0.013 mole) in dimethylsulfoxide (75 ml) was added 5 N sodium hydroxide solution (4.5 ml). To this reaction mixture, 30% hydrogen peroxide (2.63 ml) was added slowly below 25° C. Reaction mixture was stirred at ambient temperature for 6 hours. Aqueous solution of sodium sulfite (2.1 in 150 ml water) was added to the reaction mixture. The reaction mixture was extracted with ethyl acetate. The combined ethyl acetate layer was extracted 2N hydrochloric acid. The aqueous layer was neutralized with sodium bicarbonate and extracted the product in ethyl acetate. The organic layer was washed with saturated sodium bicarbonate solution followed by brine wash and dried over anhydrous sodium sulfate. The solvent was evaporated under reduced pressure, and the residue was dissolved in ethyl acetate. The resulting solution was cooled to 5° C. and filtered to get 4.51 g of (I) as solid.

The invention claimed is:

1. A process for the synthesis of Silodosin (Compound of Formula I)

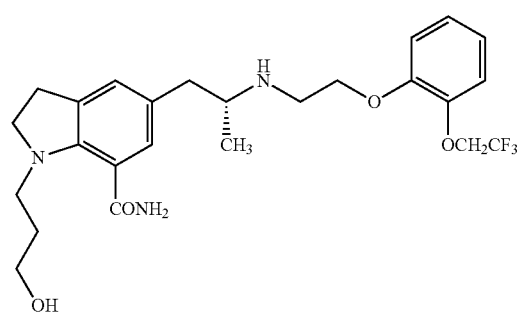

comprising reductive amination of a compound of Formula (VII) and a compound of Formula (VIII) in a suitable solvent using a reducing agent

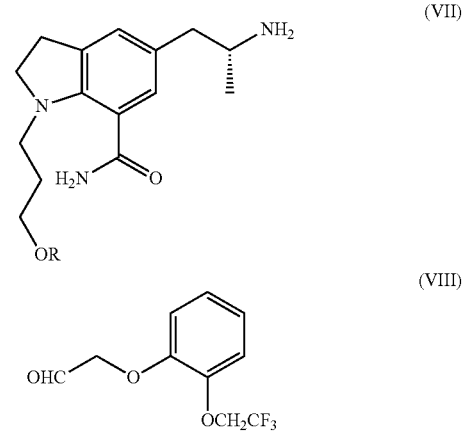

wherein R is hydrogen, tert-butyldimethylsilyl, allyl, benzyl, propargyl or trimethylsilyl.

2. The process according to claim 1, wherein the reducing agent is selected from the group comprising sodium borohydride, sodium cyanoborohydride, lithium borohydride, palladium on carbon and Raney nickel.

3. A process for the synthesis of Silodosin (Compound of Formula I)

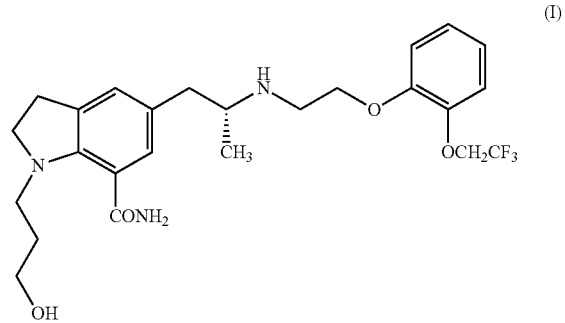

comprising reductive amination of a compound of Formula (VIII) and a compound of Formula (XV) in a suitable solvent using a reducing agent

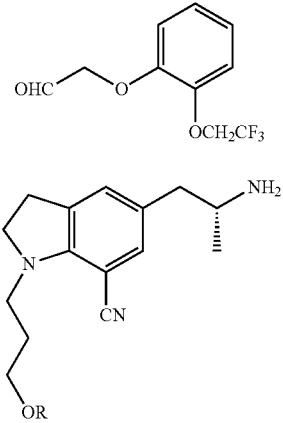

wherein R is hydrogen, tert-butyldimethylsilyl, allyl, benzyl, propargyl or trimethylsilyl.

4. The process according to claim 3, wherein the reducing agent is selected from the group comprising sodium borohydride, sodium cyanoborohydride, lithium borohydride, palladium on carbon and Raney nickel.

5. A process for the preparation of Silodosin (I)

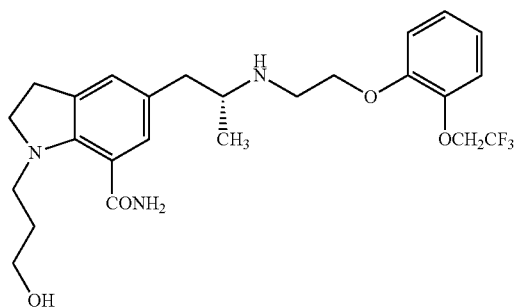

(I) comprising:

a. stirring Benzoic acid 3-[5(R)-(2-amino-propyl)-7-cyano-2,3-dihydro-indol-1-yl]-propyl ester, a weak organic acid, an alcohol solvent and a compound, [2-(2,2,2-Trifluoro-ethoxy)-phenoxy]-acetaldehyde at 25-40° C for 1-2 hours;
b. adding a reducing agent to the reaction mixture of step a and stirring for about 1-2 hours;
c. stirring the reaction mixture of step b at 35-45° C for about 2-3 hours;
d. concentrating the reaction mixture of step c by evaporating the solvent under reduced pressure;
e. acidifying the residue of step d with mineral acid;
f. extracting product in ethyl acetate followed by concentration to obtain a compound of formula (XVI) as an oil wherein R is hydrogen, tert-butyldimethylsilyl, allyl, benzyl, propargyl or trimethylsilyl

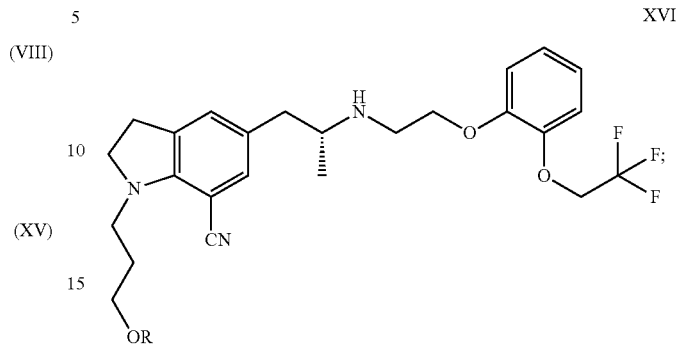

g. adding methanol and aqueous sodium hydroxide solution to the oil of step f and stirring for six hours;
h. adding water and extracting a product in an organic solvent;
i. concentrating extract of step h to yield a compound of formula (XVII)

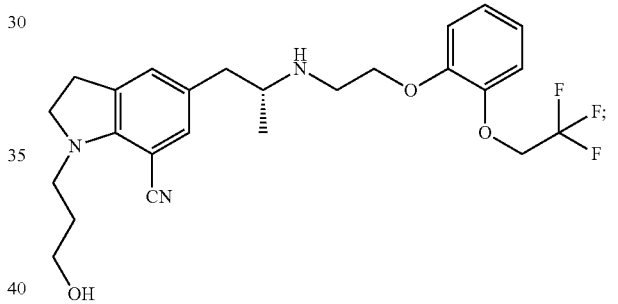

j. adding DMSO, 5N sodium hydroxide solution, 30% Hydrogen Peroxide to compound of formula (XVII) followed by stirring at ambient temperature for six to eight hours;
k. quenching reaction mixture in sodium sulfite solution;
l. extracting a product in ethyl acetate followed by acidification with 2N HCl;
m. neutralizing an aqueous layer with sodium bicarbonate;
n. extracting a product in ethyl acetate; and
o. concentrating the extract of step n under reduced pressure to obtain a solid residue followed by recrystallization in ethyl acetate to yield Silodosin (I).

6. The process according to claim 5, wherein the weak organic base in step (a) is selected from the group acetic acid, trifluoro acetic acid and formic acid.

7. The process according to claim 5, wherein the alcohol solvent in step (a) is selected from the group of lower alcohol such as methanol, ethanol, propanol, Isopropanol and tertiary butanol.

8. The process according to claim 5, wherein the reducing agent in step (b) is selected from the group of alkali borohydride, alkali cyanoborohydride, raney nickel, and Palladium on carbon.

9. A process for the preparation of Silodosin (I)

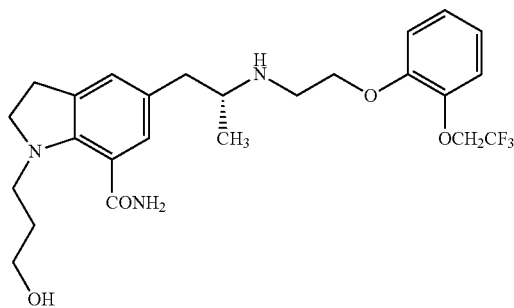

(I) comprising:
  a) stirring Benzoic acid 3-[5(R)-(2-amino-propyl)-7-cyano-2,3-dihydro-indol-1-yl]-propyl ester, DMSO, 30% Hydrogen peroxide and 5N sodium hydroxide solution for 2-4 hrs;
  b) adding water and extracting a product in an organic solvent;
  c) concentrating the organic solvent to yield a residue;
  d) adding a weak organic acid, an alcohol solvent and a compound, [2-(2,2,2-Trifluoro-ethoxy)-phenoxy]-acetaldehyde to the residue of step (c) at 25-40° C and continue stirring for about 1-2 hours;
  e) adding a reducing agent to the reaction mixture of step (d) and stirring for about 1-2 hours;
  f) stirring the reaction mixture of step (e) at 35-45° C. for about 2-3 hours;
  g) concentrating the reaction mixture of step (f) by evaporating the solvent under reduced pressure;
  h) adding aqueous mineral acid to the reaction mixture of step (g);
  i) extracting the reaction mixture of step (h) into an organic solvent;
  j) concentrating the extraction of step (i) under reduced pressure to obtain a second residue; and
  k) purifying the second residue of step (j) to yield Silodosin (I).

10. The process according to claim 9, wherein the reducing agent is alkali cyanoborohydride.

11. The process according to claim 9, in step (a) wherein the aprotic polar organic solvent is selected from dimethyl formamide, N-methyl pyrrolidone, acetonitrile, and dimethyl sulfoxide.

12. The process according to claim 9, in step (a) wherein the oxidizing agent is selected from hydrogen peroxide.

* * * * *